United States Patent

Shibata et al.

[11] Patent Number: 5,112,471
[45] Date of Patent: * May 12, 1992

[54] ION SELECTIVE ELECTRODE

[75] Inventors: Yasuhisa Shibata, Naka; Naoto Oki; Satoshi Ozawa, both of Hitachi; Hiroyuki Miyagi, Kokubunji, all of Japan

[73] Assignee: Hitachi, Ltd., Tokyo, Japan

[*] Notice: The portion of the term of this patent subsequent to Jun. 26, 2007 has been disclaimed.

[21] Appl. No.: 526,782

[22] Filed: May 18, 1990

Related U.S. Application Data

[63] Continuation of Ser. No. 343,275, Apr. 26, 1989, abandoned.

[30] Foreign Application Priority Data

Apr. 28, 1988 [JP] Japan .................. 63-103935
Jul. 18, 1988 [JP] Japan .................. 63-178374

[51] Int. Cl.$^5$ .......................... G01N 27/26
[52] U.S. Cl. .................. 204/418; 204/153.13; 204/153.15
[58] Field of Search .............. 204/418, 153.13, 153.15

[56] References Cited

U.S. PATENT DOCUMENTS

| | | | |
|---|---|---|---|
| 4,519,891 | 5/1985 | Sugahara et al. | 204/418 |
| 4,810,331 | 3/1989 | Garrison et al. | 204/418 |
| 4,936,975 | 6/1990 | Shibata et al. | 204/418 |

FOREIGN PATENT DOCUMENTS

| | | |
|---|---|---|
| 300364 | 7/1988 | European Pat. Off. |
| 56-63246 | 5/1981 | Japan . |
| 57-77952 | 5/1984 | Japan . |
| 59-137851 | 8/1984 | Japan . |
| 2062245 | 10/1980 | United Kingdom . |

OTHER PUBLICATIONS

D. Wegman et al., "Microchimica Acts", (Wein), 1984 III, 1.

Primary Examiner—John Niebling
Assistant Examiner—Bruce F. Bell
Attorney, Agent, or Firm—Fay, Sharpe, Beall, Fagan, Minnich & McKee

[57] ABSTRACT

The present invention provides an ion selective electrode for anions such as $Cl^-$ and cations such as $Ca^{2+}$ which has a sensitive membrane comprising a polymer material and containing an ion sensitive material and a plasticizer. In thins ion selective electrode, the ion sensitive material is an ion exchanger such as a quaternary ammonium salt, a quaternary phosphonium salt or an organic phosphate and the plasticizer is a compound having the formula (1):

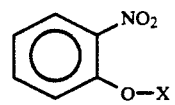

wherein X represents an alkyl group, a phenyl group or a phenyl group to which a functional group bonds. As the plasticizer there may also be used a mixture of the compound of the formula (1) with an alcohol compound such as an alcohol having a dielectric constant of 10 or less and containing 10 or more carbon atoms or an ester compound.

14 Claims, 5 Drawing Sheets

N = 22
AUE1 = 104.7 +- (9.3)
AUE2 = 100.3 +- (9.3)
R    = 0.9808
Y    = 0.98x+(-2.61)
SYX  = 1.91

FIG. 7

ION SELECTIVE ELECTRODE

This is a continuation-in-part of co-pending application Ser. No. 221,291, filed on July 19, 1988, U.S. Pat. No. 4,936,975.

BACKGROUND OF THE INVENTION

1. Field of the Invention

The present invention relates to an ion selective electrode and more particularly to an ion selective electrode which has a polymer material as a support and which is suitable for use in analysis of anions such as chloride ion, and cations such as alkali metals and alkaline earth metals, which are contained in living organisms, foods or the environment.

2. Description of Related Art

An ion selective electrode is used together with a reference electrode, and when both are allowed to contact, for example, body fluid, an electromotive force depending on the objective ion concentration is generated between the electrodes and an operational processing is carried out based on the output power to measure the objective ion concentration. The ion selective electrode used in this way includes a solid electrode comprising silver chloride and silver sulfide and a polymer supporting electrode comprising a polymer in which an ion exchanger or neutral carrier is dispersed as a sensitive material. As the latter ion selective electrode which comprises an ion exchanger as a sensitive material, in the conventional chloride ion selective electrode, a sensitive membrane is composed of an ion sensitive material, a plasticizer and a base material. An organic compound having a relatively high dielectric constant of at least 15 is used as a part of the plasticizer in order that the ion sensitive material in the sensitive membrane is dissociated to enhance solubility and to promote ion dissociation equilibration, whereby the electrode is operated as a liquid membrane type ion selective electrode as disclosed in Japanese Patent Kokai (Laid-Open) No. 59-137851. However, investigation of the organic compound as a plasticizer used to promote ion dissociation equilibration of an ion exchanger which is a sensitive material in the sensitive membrane has been insufficient. Therefore, when the conventional plasticizer is used, impedance of the liquid membrane type ion selective electrode which contains a straight chain alcohol which readily crystallizes at low temperatures increases in use over a long period of time and the response speed is apt to decrease.

Furthermore, as a chloride ion selective electrode used for analysis of chloride ions, for example, in living body fluid, there has been employed a solid membrane type electrode comprising silver chloride and silver sulfide or a polymer supporting liquid membrane type electrode in which an ion exchanger is supported as a sensitive material in a synthetic polymer supporting membrane such as polyvinyl chloride. The former electrode suffers from the problem that obstruction by halogen ions such as bromide ion or sulfide ions is great. On the other hand, the latter electrode also suffers from the problems that errors in measurement are apt to occur due to oleophilic ions trapped in the sensitive membrane and life of electrode is shortened due to a dissolving out of the ion exchanger used as a sensitive material from sensitive membrane or adsorption of protein and the like to the surface of sensitive membrane. Under the circumstances, attempts have been made to solve these problems with polymer supporting liquid membrane type electrodes. For example, Japanese Patent Kokai (Laid-Open) No. 56-63246 proposes the use of methyltridodecylammonium chloride as a sensitive material and n-tetradecyl alcohol (straight chain aliphatic alcohol of 14 carbon atoms) as a plasticizer in order to reduce obstruction due to adsorption of protein and the like. Japanese Patent Kokai (Laid-Open) No. 59-137851 has proposed to use dimethyldioctadecylammonium chloride as a sensitive material and a mixture of a straight chain aliphatic alcohol and o-nitrophenyloctyl ether as a plasticizer in order to improve responsivity and reduce errors in measurement. Furthermore, it has been disclosed that n-dodecyl alcohol (carbon number: 12 and melting point: 23.5° C.) is added in addition to n-tetradecyl alcohol (carbon number: 14 and melting point: 38.3° C.) as the straight chain aliphatic alcohol in order to increase solubility of the sensitive material and decrease crystallization of the membrane material. Moreover, according to the process disclosed in Mikrochimica Acta, (Wein) 1984 III, 1, tetradodecylammonium chloride is used as a sensitive material in order to improve selectivity over hydrogen-carbonate ion contained in blood. However, the chloride ion selective electrode in which the above sensitive material is used is deteriorated in selectivity over oleophilic anion. As mentioned above, conventional methods for improvement have tried to solve the problems by changing the structure or kind of sensitive material and plasticizer. However, in the case of a chloride ion selective electrode according to the conventional methods, if it is attempted to control the selectivity over oleophilic anions, selectivity over the hydrophilic anions such as hydrogencarbonate ions decreases. On the contrary, if it is attempted to improve the selectivity over hydrophilic anions such as hydogencarbonate ions, selectivity over oleophilic anions is extremely deteriorated. Therefore, in order to reduce errors in measurement and to improve the accuracy of a polymer supporting liquid membrane type chloride ion selective electrode, it is important to improve selectivity over both the hydrophilic anions and the oleophilic anions. It is also important for functioning as a liquid membrane type electrode to select a plasticizer which can increase the solubility of the sensitive material and reduce the crystallization of the membrane material, and which is stably maintained in the sensitive membrane.

In the conventional techniques, namely, in the conventional polymer supporting liquid membrane type chloride ion selective electrode where a straight chain aliphatic alcohol is used as a plasticizer, examination on carbon number of the aliphatic alcohol has been insufficient. Especially when tetraalkylammonium salt is used as a sensitive material, there is the problem that if the carbon number of aliphatic alcohol which is a plasticizer is increased, the aliphatic alcohol is readily crystallized and dissolves the sensitive material with difficulty and thus the impedance of the electrode increases resulting in a decrease of response speed. On the other hand, there is also the problem that if the carbon number of the aliphatic alcohol is decreased, water-solubility thereof increases and hence the response to potential becomes unstable and the performance of the electrode cannot be maintained for a long time. As mentioned above, when a dimethyldioctadecylammonium salt is used as a sensitive material, there is the known technique (Japanese Patent Kokai (Laid-Open) No. 59-137851) which uses mixtures of straight chain aliphatic alcohols different in carbon number as a plasticizer, but it is difficult to apply this known technique in the case of using a tetraalkylammonium salt which is very low in solubility as a sensitive material. This is because the known technique uses aliphatic alcohols different by two in carbon number and so the difference in properties of them is too great to solve all of the above problems.

SUMMARY OF THE INVENTION

The object of the present invention is to provide an ion selective electrode used for detection of anions such as chloride ions, cations such as alkali metal ions' or alkaline earth metal ions' which is low in impedance, fast in response, stable in response to potential and able to maintain its performances for a prolonged period of time due to its high slope sensitivity.

According to the present invention, the above object can be attained by containing an ion sensitive material and a plasticizer in a sensitive membrane comprising a polymer and using an ion exchanger as the ion sensitive material, and a compound having the formula (1):

(1)

wherein X represents an alkyl group, a phenyl group or a phenyl group to which a functional group bonds, as a plasticizer.

The above object can also be attained by using an ion exchanger as the ion sensitive material and an alcohol compound or an ester compound in addition to the above-mentioned compound of the formula (1) as the plasticizer.

DETAILED DESCRIPTION OF PREFERRED EMBODIMENTS

The polymer supporting liquid membrane type, ion selective electrode of the present invention contains as a main element a sensitive membrane comprising a polymer material as a base material, a plasticizer and an ion sensitive material.

The kinds of ions to be detected by the ion selective electrode of the present invention are cations such as, for example, $Na^+$, $K^+$, and $Ca^{2+}$ and anions such as, for example, $Cl^-$. The ion selective electrode of the invention is suitable especially for the detection of chloride ions, and so explanation is made herein about use of the electrode for detection of chloride ions, but the present invention should not be limited thereto.

The polymer material used as a support may be any of those which are commonly used in this field and includes, for example, polyvinyl chloride, polycarbonate, silicone rubber and epoxy resin.

If the content of the polymer material in the sensitive membrane is less than 25 wt% relative to other components, the mechanical strength of the sensitive membrane is much deteriorated. On the other hand, if it is more than 60 wt %, impedance of the membrane increases and it becomes difficult to obtain stable performance of the electrode. Therefore, the content of the polymer material is preferably 25-60 wt %.

As the ion sensitive material used in the present invention, there may be used ion exchangers such as quaternary ammonium salts, quaternary phosphonium salts and specific organic phosphate salts.

When quaternary ammonium salt is used as a sensitive material, the following 4 kinds can be mentioned.

Type (1) $[(CH_3)_3R\ N]^+X^-$
Type (2) $[(CH_3)_2R_2N]^+X^-$
Type (3) $[CH_3\ R_3N]^+X^-$
Type (4) $[R_4N]^+X^-$ wherein R represents an aliphatic alkyl group of 2 or more carbon atoms and $X^-$ represents an anion.

Type (1) is lower than the other three in oleophilicity of the compound per se and is not preferred as a sensitive material for a chloride ion selective electrode regarding stability and life. On the other hand, since the compounds of types (2), (3) and (4) are far more the carbon number than the compound of type (1) owing to an increase in the number of the alkyl group R, oleophilicity is increased and hence they have the possibility to be used as a sensitive material for the chloride ion selective electrode. In fact, compounds of types (2) and (3) are generally used.

In the tetraalkylammonium salt of type (4) which contains four alkyl groups, bulky four alkyl groups are present around the nitrogen atom and so it is considered that the nitrogen atom of this ammonium salt is more difficult to be attacked by bulky anions than the ammonium salts of types (1)-(3) from the point of molecular structure. Therefore, it is considered that a chloride ion selective electrode containing the compound of type (4) as a sensitive material is improved over the chloride ion selective electrodes containing the compounds (1)-(3) as a sensitive material in selectivity over various bulky anions such as hydrophilic sulfate ion and hydrogencarbonate ion and oleophilic perchlorate ion and thiocyanate ion. However, when the tetraolkylammonium salt is used as a sensitive material of a chloride ion selective electrode, selection of plasticizers which dissolve the ammonium salt and form a state of ionization into cation and is severely limited. Therefore, unless a suitable plasticizer is used, there may result in electrodes insufficient in basic performances such as responsivity and sensitivity. Especially, with an increase in carbon number of the alkyl group of the sensitive material, the solubility of the compound in various plasticizers is much lower and its use as a plasticizer is further limited. For these reasons, ion selective electrodes having basic performances such as selectivity and responsivity sufficient to analyze chloride ions in a living body fluid have not yet been found and at present any practical chloride ion selective electrode containing type (4) has not been obtained. Therefore, in the case of using the compound of type (4), the combination of sensitive material and plasticizer, and the optimization of the compositions are important.

In the present invention, a tetraalkylammonium salt is used as a quaternary ammonium salt type ion exchanger which is a chloride ion sensitive material. Such quaternary ammonium salts are preferably tetraalkylammonium salts having four alkyl groups, each of which has 10-24 carbon atoms such as tetradecylammonium salts, tetracetylammonium salts and tetraoctadecylammonium salts.

If the carbon number of the alkyl group is less than 10, selectivity over various ions is inferior and if more than 24, solubility of the organic compound is inferior.

The content of tetraoctadecylammonium salt dispersed in a sensitive membrane is properly 5-30 wt% considering responsivity, selectivity and reduction of impedance of the membrane. For these reasons, the range of 5-30 wt% is also preferred in the case of using other tetraalkylammonium salts as a sensitive material.

Hitherto, when a straight chain aliphatic alcohol is used as a plasticizer, n-tetradecyl alcohol of 14 carbon atoms has sometimes been used. Further, when it is difficult to dissolve the sensitive material only by this alcohol, an organic compound of higher dielectric constant for example, o-nitrophenyloctyl ether is used in admixture. However, the above tetraalkyl type sensitive materials are low in solubility in n-tetradecyl alcohol and even with the addition of o-nitrophenyloctyl ether, it is soluble with difficulty especially at a low temperature, and when this was applied to electrodes, problems such as increase of impedance and reduction of response speed often occurred. It is known for solving these problems to further add n-dodecyl alcohol less by two in carbon number to increase solubility of sensitive material and reduce crystallization of other materials of the membrane as mentioned above. However, the straight chain aliphatic alcohol less by 2 in carbon number is smaller by about 1 in log P (parameter for oleophilicity) which is an indication for oleophilicity and greater by about one figure in partition in water. That is, since straight chain aliphatic alcohols less in carbon number readily dissolve out into a sample solution, stability of electrode potential is low and besides the especially added alcohol dissolves out in a short time and the effect cannot be retained. This tendency becomes greater in measurement of blood serum. Therefore, a straight chain aliphatic alcohol of 13 carbon atoms less by one than 14 carbon atoms of n-tetradecyl alcohol is employed. In this case, the solubility of the sensitive material can be increased and crystallization of other materials of membrane can be reduced, and besides decrease of oleophilicity can be minimized. Thus, an electrode low in impedance and fast in response is obtained. In addition, no problems of unstable potential of the electrode and reduction of the electrode performance in a short time occur.

When operation at around room temperature is desired a, combination of n-tetradecyl alcohol and n-tridecyl alcohol is used as a plasticizer of the aliphatic alcohol having a low dielectric constant, but it should not be limited thereto. For other operation temperatures, there are obtained good results with use of a combination of two aliphatic alcohols which have a dielectric constant of 10 or less and have 10-40 carbon atoms, and which are different by one in the number of carbon atoms from each other or are different by 13° C. or lower in melting point. From the points of responsivity and selectivity as a chloride ion selective electrode, the content of the two aliphatic alcohols having a low dielectric constant in sensitive membrane is suitably 11-60 wt % in total.

When only the straight chain aliphatic alcohol of low dielectric constant is present as a plasticizer in a sensitive membrane, a chloride ion selective electrode having this membrane is insufficient in responsivity and stability. This is because the plasticizers used are both low in dielectric constant. This is insufficient as the condition for allowing the equilibrium in ion dissociation reaction of the following formula (2) in proceed to the right directions as much as possible.

$$(C_{18}H_{37})_4N\ X \rightarrow [(C_{18}H_{37})]^+ + X^- \qquad (J2)$$

In one preferred embodiment, an additional one plasticizer is present in the sensitive membrane, namely, the plasticizer comprises a mixed system of three plasticizers. That is, an organic compound having a high dielectric constant of 15 or higher and having high oleophilicity is allowed to coexist. By the coexistence of this plasticizer, the equilibrium of the above formula (2) shifts to the right direction, resulting in superior performance as a chloride ion selective electrode. As the organic compound of high dielectric constant, there may be used not only o-nitrophenyloctyl ether, but also nitrobenzene and derivatives thereof (o, m, p-nitrotoluene, etc.), acetophenone and derivatives thereof and the like. Content of the compound in a sensitive membrane is suitably 5-20 wt %.

As one embodiment of the present invention polyvinyl chloride is used as a polymer material on which the plasticizer or the sensitive material is supported. Other polymer materials usable include, for example, polycarbonate, silicone rubber and epoxy resin. When the content of the polymer material in sensitive membrane 4 is less than 25 wt % relative to other components, mechanical strength of sensitive membrane 4 is extremely deteriorated. On the other hand, when more than 60 wt %, impedance of the membrane increases and it is difficult to obtain stable electrode performance. Therefore, the content of the polymer material is preferably 25-60 wt %.

For attaining the object of the present invention, it is preferred to use an organic compound having a dielectric constant of 40 or higher that is sparingly soluble in having a sensitive membrane of a polymer material which contains an ion sensitive material and a plasticizer.

Such plasticizer includes, for example, 2-nitrophenylphenyl ether or a halogen derivative thereof. It is effective to use the 2-nitrophenylphenyl ether or halogen derivative thereof in the sensitive membrane in an amount of 1-30 wt %.

An ion exchanger may be used as ion sensitive material and a halogen derivative of 2-nitrophenylphenyl ether may be used as a plasticizer in this sensitive membrane. Furthermore, it is also possible to use a quaternary ammonium salt as an ion sensitive material and 2-fluoro-2'-nitrodiphenyl ether as a plasticizer in this sensitive membrane. Moreover, use of tetraalkylammonium salt as this quaternary ammonium salt is effective.

The content of 2-fluoro-2'-nitrodiphenyl ether in the sensitive membrane is preferably 1–40 wt % when the selectivity of the chloride ion selective electrode, and the impedance and film formability of the sensitive membrane are considered.

This sensitive membrane may contain a tetraalkylammonium salt as an ion sensitive material and a straight chain alcohol of 10 or more carbon atoms and 2-nitrophenylphenyl ether or a halogen derivative thereof as a plasticizer. It is effective that the straight chain alcohol of 10 or more carbon atoms comprises two straight chain alcohols different by one in carbon number from each other and it is further effective that the straight chain alcohols different by one in carbon number and are n-tridecyl alcohol and n-tetradecyl alcohol.

The tetraalkylammonium salt preferably has alkyl groups each of which has 10–24 carbon atoms. Furthermore, it is effective that this sensitive membrane contains 25–60 wt % of a polymer material, 5–30 wt % of a tetraalkylammonium salt as an ion sensitive material, 1–20 wt % of n-tridecyl alcohol, 10–40 wt % of n-tetradecyl alcohol and 1–30 wt % of 2-fluoro-2'-nitrodiphenyl ether as plasticizers.

This sensitive membrane may contain an organic phosphate salt as an ion sensitive material and a halogen derivative of 2-nitrophenylphenyl ether as a plasticizer.

The aliphatic alcohol used is not necessarily of straight chain, but may be a branched chain aliphatic alcohol. Since such a branched chain aliphatic alcohol is generally lower in melting point than a straight chain alcohol, good results can be obtained by increasing the carbon number in order to obtain good electrode characteristics at around room temperature as mentioned hereinbefore. The branched chain aliphatic alcohol is higher in oleophilicity than straight chain aliphatic alcohol and higher in stability in membrane.

The plasticizer used in the present invention plasticizes the base material comprising a polymer material and further promotes dissociation and dissolution of the ion sensitive material and accelerates ion dissociation equilibration. By using an organic compound having a dielectric constant of 40 or more as the plasticizer, dissociation equilibration of ion sensitive material in the sensitive membrane is accelerated and besides, since the plasticizer is sparingly soluble in water and is difficult to be dissolved in living body fluid, impedance of the ion selective electrode is not increased.

2-Nitrophenylphenyl ether and halogen derivatives thereof are preferred as a plasticizer because they are organic compounds having a dielectric constant of 40 or more and are sparingly soluble in water. It is more effective to contain either 2-nitrophenylphenyl ether or a halogen derivative thereof in an amount of 1–30 wt % in a sensitive membrane. When the content of this plasticizer is less than 1 wt %, response time is prolonged and when more than 30 wt %, the contents of other components decrease to cause deterioration in strength of sensitive membrane.

Furthermore, the ion sensitive material is easily ion dissociation equilibrated and the plasticizer accelerates ion dissociation equilibration of the ion sensitive material and does not dissolve out into living body fluid when an ion exchanger is used as the ion sensitive material and a halogen derivative of 2-nitrophenylphenyl ether is used as a plasticizer, furthermore, when a quaternary ammonium salt which is an ion exchanger is used as the ion sensitive material and 2-fluoro-2'-nitrodiphenyl ether as the plasticizer and also when a tetraalkylammonium salt is used as the quaternary ammonium salt.

Furthermore, the ion sensitive material and the plasticizer act as mentioned above when a tetraalkylammonium salt is used as the ion sensitive material and a straight chain alcohol of 10 or more carbon atoms and either 2-nitrophenylphenyl ether or a halogen derivative thereof as the plasticizers. Straight chain alcohols of less than 10 carbon atoms are easily soluble in water and hence those of 10 or more carbon atoms are preferred.

Moreover, it is more effective for impedance of the electrode to use two straight chain alcohols differing by one in carbon number from each other as the straight chain alcohol of 10 or more carbon atoms and particularly to use n-tridecyl alcohol and n-tetradecyl alcohol as these two straight chain alcohols. In this case, crystallization of plasticizer in sensitive membrane can be reduced.

Furthermore, it is effective that the sensitive membrane contains 25–60 wt % of a polymer material, 5–30 wt % of a tetraalkylammonium salt as the ion sensitive material and 1–20 wt % of n-tridecyl alcohol, 10–40 wt % of n-tetradecyl alcohol and 1–30 wt% of 2-fluoro-2'-nitrodiphenyl ether as the plasticizers. If the contents of these components are too high or too low, ion selectivity of the electrode decreases.

A sensitive membrane which selects cations is formed by using an organic phosphate salt as an ion sensitive material and a halogen derivative of 2-nitrophenylphenyl ether as a plasticizer in a sensitive membrane.

The present invention has the construction as explained above and accordingly exhibits the following effects.

By using an organic compound having a dielectric constant of 40 or more and sparingly soluble in water as a plasticizer contained in the sensitive membrane of ion selective electrode, solubility of the ion sensitive material is enhanced and ion dissociation equilibration is accelerated and the plasticizer is retained since the plasticizer dissolves in living body fluid with difficulty. Therefore, impedance of the ion selective electrode does not increase in use over a prolonged period and thus this ion selective electrode is excellent in ion selectivity and responsivity.

The same effects as above are obtained for the same reasons as above by using either 2-nitrophenylphenyl ether or its halogen derivative as a plasticizer and furthermore by adding either one of them in an amount of 1–30 wt % in sensitive membrane.

In addition, the same effects as above are obtained for the same reasons by using an ion exchanger as an ion sensitive material and a halogen derivative of 2-nitrophenylphenyl ether as a plasticizer, further, by using a quaternary ammonium salt which is an ion exchanger as the ion sensitive material and 2-fluoro-2'-nitrodiphenyl ether as the plasticizer, and furthermore, by using a tetraalkylammonium salt as the quaternary ammonium salt.

Moreover, the same effects as above are obtained by using tetraalkylammonium salt as the ion sensitive material and a straight chain alcohol of 10 or more carbon atoms and either 2-nitrophenylphenyl ether or its derivative as plasticizers, further, by using two straight chain alcohols differing by one in carbon number from each other as the straight chain alcohols of 10 or more carbon atoms and furthermore, by using n-tridecyl alcohol and n-tetradecyl alcohol as the two straight chain alcohols differing by one in the number of carbon atoms. Use of the two straight chain alcohols is more effective with respect to impedance of the electrode and to reduce crystallization of the plasticizer in the sensitive membrane.

Further, the same effects are obtained by using a tetraalkylammonium salt having alkyl groups each of which has 10-24 carbon atoms as the tetraalkylammonium salt as the ion sensitive material.

Further, the same effects are obtained when the sensitive membrane contains 25-60 wt % of a polymer material, 5-30 wt % of a tetraalkylammonium salt as an ion sensitive material and 1-20 wt % of n-tridecyl alcohol, 10-40 wt % of n-tetradecyl alcohol and 1-30 wt % of 2-fluoro-2'-nitrodiphenyl ether as plasticizers.

Moreover, the same effects are obtained by using an organic phosphate salt as an ion sensitive material and a halogen derivative of 2-nitrophenylphenyl ether as a plasticizer in a sensitive membrane since a sensitive membrane which selects cations is formed and the dissociation equilibration of the ion sensitive material is promoted.

Since the ion selective electrode of the present invention does not show an increase of impedance during its use over a long time has fast response speed and further is excellent in ion selectivity, when this electrode is used as a detector of an analyzer for electrolyte in living body fluid, there are the advantages that it can be used stably for a long time and examination of many living body fluids can be performed for a certain period.

According to the present invention, there are provided the advantages that the solubility of the sensitive material in a sensitive membrane can be enhanced and crystallization of the membrane component can be reduced and so that a chloride ion selective electrode can be obtained which is low in impedance, fast in response speed and stable in electrode potential, and can maintain electrode performance for a long time, by using a quaternary ammonium salt or a quaternary phosphonium salt as a chloride ion sensitive material and two aliphatic alcohols differing by one in carbon number or two aliphatic alcohols by 13° C. or lower in melting point as plasticizers, and thus optimizing the composition of the membrane.

Further, in the ion selective electrode of the present invention, the ion sensitive material in the sensitive membrane is easily dissociation equilibrated and the plasticizer accelerates the dissociation equilibration and is sparingly soluble in a living body fluid. Hence, impedance of the electrode does not increase during its use over a long time. Therefore, an analyzer for electrolytes in living body fluids containing this electrode as a detector can be used stably for a prolonged period.

Embodiments of the present invention will be explained referring to FIGS. 1-7.

The ion selective electrode is a chloride ion selective electrode in which a quaternary ammonium salt is used as an ion sensitive material.

Figure 1:
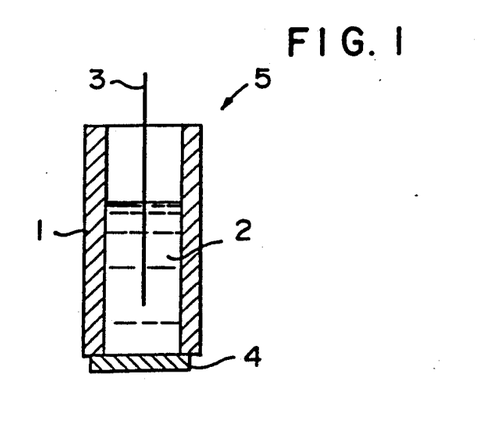
FIG. 1 is a schematic cross-sectional view of the chloride ion selective electrode of the present invention.

The electrode structure includes a stick type electrode as shown in FIG. 1 and a flow-through type electrode which analyzes flowing living body fluid. The present invention can be applied to both of them.

Electrode cylinder 1 contains an internal solution 2 containing 10 mmol/l of NaCl and an internal electrode 3 comprising Ag having AgCl formed as the surface layer and immersed in the internal solution 2. Sensitive membrane 4 is allowed to adhere to the end of electrode cylinder 1 with a solvent such as tetrahydrofuran. This sensitive membrane 4 contains a polymer material such as polyvinyl chloride and therein are further dispersed an ion sensitive material and a plasticizer in optimum weight concentrations, respectively.

In the present invention, tetraalkylammonium salts having alkyl groups each of which has 10-24 carbon atoms such as tetracetylammonium chloride and tetraoctadecylammonium chloride which are quaternary ammonium salt type ion exchangers are used as the chloride ion sensitive material. Tetraalkylphosphonium salts may also be used in place of the above tetraalkylammonium salts.

Figure 3:
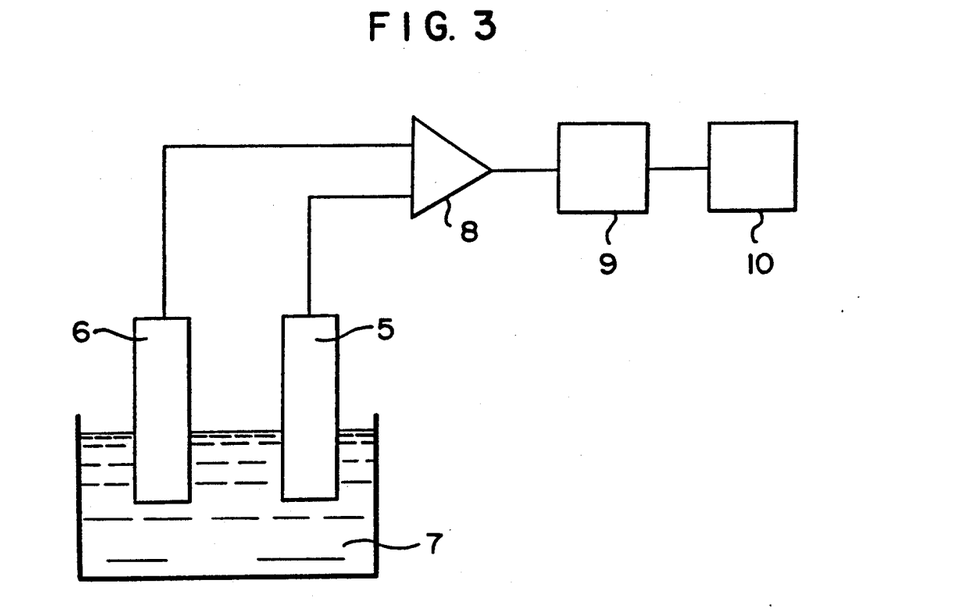
FIG. 3 is a flow chart which shows construction of an analyzer for an electrolyte contained in a living body fluid which is provided with the ion selective electrode of the present invention as a detector.

An analyzer for electrolytes in living body fluids was constructed in which an ion selective electrode containing 2-nitrophenylphenyl ether or its halogen derivative as a plasticizer based on the present invention was used. As shown in FIG. 3, ion selective electrode 5 is immersed in sample solution 7 together with reference electrode 6. The ion selective electrode 5 used herein may be of the cation selective type or anion selective or may be a combination of the two as long as the electrode contains the above plasticizer. An electromotive force corresponding to the desired ion concentration is generated between the electrodes and is operated by operator 9 based on the signal amplified by amplifier 8. The desired ion concentration is displayed in display part 10.

An analyzer for an electrolyte has an ion selective electrode fast in response that can improve the quantity to be treated per unit time and enhance the speed of analysis.

EXAMPLE 1

In this example, a tetraoctadecylammonium salt was used as a chloride ion sensitive material. 15 wt % of this ion sensitive material, 25 wt % of n-tetradecyl alcohol and 5 wt % of n-tridecyl alcohol which are straight chain and 5 wt % of 2-fluoro-2'-nitrodiphenyl ether (dielectric constant: about 50) which is an organic compound of high dielectric constant as plasticizers and 50 wt % of polyvinyl chloride as a polymer material which is a base material were weighed and mixed and dissolved in a solvent (tetrahydrofuran) to prepare a homogeneous solution. Then, the solvent was removed by evaporation to make a sensitive membrane in a dispersed state. This sensitive membrane was punched into suitable size depending on the size of electrode cylinder 1 of FIG. 1 and adhered to the end of electrode cylinder 1.

EXAMPLE 2

In this example, a calcium ion selective electrode was prepared in which bis[di{p-(1,1,3,3-tetramethylbutyl)-phenyl}phosphato]calcium (II) which is an organic phosphate salt was used as ion sensitive material and 2-nitrophenylphenyl ether and 2-fluoro-2'-nitrodiphenyl ether were used as plasticizer. With use of any of these plasticizers, the range where the desired ion concentration in a living body fluid and the corresponding output was linear was wide, namely, $10^{-6}$–$10^{-1}$ mol/l and the slope sensitivity was good, namely, 23–25 mV/dec. Further, the 95% response time was fast, namely, 10 seconds or less, and the selectivity coefficient for magnesium ions was about 0.001. Thus, it is seen that the above calcium ion selective electrode is able to be put to practical use.

As mentioned above, according to this example, both the cation selective electrode and the anion selective electrode were low in impedance and further, ion selective electrodes having superior responsivity and selectivity were obtained.

COMPARATIVE EXAMPLE 1

Figure 2:
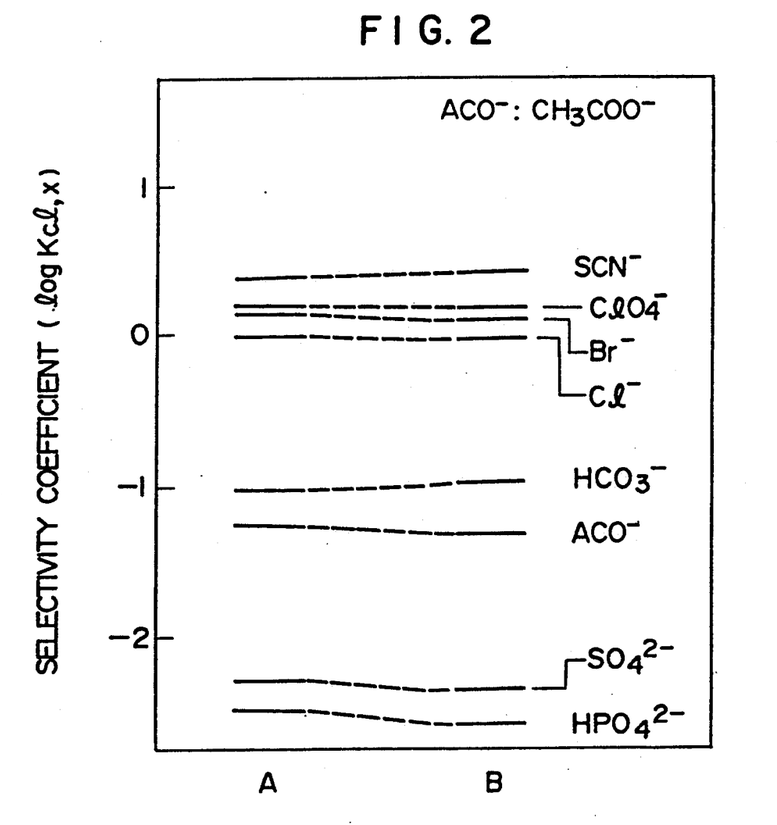
FIG. 2 is a graph which shows the selectivity coefficient of a chloride ion selective electrode (A) of the present invention and that of a conventional chloride ion selective electrode (B) over various ions.

The selectivity coefficient of a chloride ion selective electrode of the present invention and that of a similar comparative ion selective electrode were measured by a single solution method (G. J. Moody and J. D. R. Thomas, "SELECTIVE ION SENSITIVE ELECTRODE", published by Merrow Publishing Co., Ltd., 1971). The results are shown in FIG. 2. This selectivity coefficient indicates the degree of obstruction by other components to the ion to be analyzed.

The comparative electrode was the same as the electrode of the present invention except that 5 wt % of orthonitrophenyloctyl ether (dielectric constant; about 24) was used as an organic compound used as a part of the plasticizer. Selectivity of the chloride ion selective electrode (A) of the present invention and that of the comparative electrode (B) over various ions was nearly the same and it was seen that selectivity did not decrease.

The results of a comparison of impedance in these electrodes are shown in Table 1. Impedance was measured by the method disclosed in D. Ammann et al, Anal. Chem. Acta, 171, p. 119 (1985).

TABLE 1

| Electrode | Impedance (MΩ) |
|---|---|
| (A) | 5–10 |
| (B) | 100–500 |

Impedance was measured by applying a potential to both surfaces of the membrane. As is clear from Table 1, the chloride ion selective electrode (A) of the present invention decreased to less than 1/10 that of the comparative electrode (B). Furthermore, 95% response time was measured using aqueous sodium chloride solutions of 10 mmol/l and 100 mmol/l. Response time of the chloride ion selective electrode (A) of the present invention was 5–10 seconds and was faster than 15–30 seconds of the comparative electrode (B).

EXAMPLE 3

In this example, tetraoctadecylammonium chloride was used as a chloride ion sensitive material. 15 wt % of this sensitive material, 25 wt % of n-tetradecyl alcohol (dielectric constant: about 4.5, melting point: 38.3° C.), 5 wt % of n-tridecyl alcohol (melting point: 30.5° C.) and 10 wt % of o-nitrophenyloctyl ether (dielectric constant: about 24) as plasticizers and 45 wt % of polyvinyl chloride as a polymer material were weighed and mixed and dissolved in a solvent (tetrahydrofuran). This solvent was removed by evaporation to form a sensitive membrane, which was punched into a suitable size depending on the size of electrode cylinder 1, shown in FIG. 1, and adhered to the end of electrode cylinder 1.

EXAMPLE 4

In this example, 15 wt % of tetraoctadecylammonium chloride as a sensitive material, 20 wt % of n-tetradecyl alcohol and 10 wt % of n-tridecyl alcohol as plasticizers of low dielectric constant, o-nitrophenyloctyl ether as a plasticizer of high dielectric constant and 45 wt % of polyvinyl chloride as a polymer material were used for composition of sensitive membrane 4. Sensitive membrane 4 was made in the same manner as in Example 3.

EXAMPLE 5

In this example, 15 wt % of tetracetylammonium chloride as a sensitive material, 28 wt % of n-tetradecyl alcohol and 2 wt % of n-tridecyl alcohol as plasticizers of low dielectric constant, 10 wt % of o-nitrophenyloctyl ether as a plasticizer of high dielectric constant and 45 wt % of polyvinyl chloride were used for composition of sensitive membrane 4. Sensitive membrane 4 was prepared in the same manner as in Example 3. The carbon number of each alkyl group of the sensitive material was 16 in this example which is less by two than in the sensitive material used in Example 3. For this reason, when a sensitive material high in solubility was used, stable electrode characteristics were obtained even with the content of n-tridecyl alcohol being about 2 wt %.

EXAMPLE 6

In this example, 15 wt % of tetraoctadecylammonium chloride as a sensitive material, 25 wt % of n-tetradecyl alcohol and 5 wt % of n-tridecyl alcohol as plasticizers of low dielectric constant, 5 wt % of o-nitrophenyloctyl ether as a plasticizer of high dielectric constant and 50 wt % of polyvinyl chloride as a polymer material were used for composition of sensitive membrane 4. Sensitive membrane 4 was made in the same manner as in Example 3.

EXAMPLE 7

In this example, 15 wt % of tetraoctadecylammonium chloride as a sensitive material, 25 wt % of 11-docosanol ($C_{10}H_{21}$—CHOH—$C_{11}H_{23}$) and 5 wt % of 11-heneicosanol ($C_{10}H_{21}$—CHOH—$C_{10}H_{21}$) as plasticizers of low dielectric constant, 10 wt % of o-nitrophenyloctyl ether as a plasticizer of high dielectric constant and 45 wt % of polyvinyl chloride were used for composition of sensitive membrane 4. Sensitive membrane 4 was prepared in the same manner as in Example 3.

COMPARATIVE EXAMPLES 2–6

The chloride ion selective electrode in Comparative Example 2 contained 15 wt % of tetraoctadecylammonium chloride as a sensitive material, 30 wt % of n-tetradecyl alcohol and 10 wt % of o-nitrophenyloctyl ether as plasticizers and 45 wt % of polyvinyl chloride as a polymer material. That is, this electrode was different from that of the present invention in that it contained only one aliphatic alcohol.

Comparative Example 3 shows a modification of the anion selective electrode disclosed in Japanese Patent Kokai (Laid-Open) No. 57-77952. This electrode contained 15 wt % of methyltridodecylammonium chloride as a sensitive material, 30 wt % of n-tetradecyl alcohol as a plasticizer and 55 wt % of polyvinyl chloride as a polymer material.

Comparative Example 4 is based on the liquid membrane type anion selective electrode shown in Example 2 of Japanese Patent Kokai (Laid-Open) No. 59-137851. This membrane contained 15 wt % of dimethyldioctadecylammonium chloride as a sensitive material, 30 wt % of n-tetradecyl alcohol and 10 wt % of o-nitrophenyloctyl ether as plasticizers and 45 wt % of polyvinyl chloride as a polymer material.

Comparative Example 5 shows a modification of the liquid membrane type anion selective electrode shown in Example 3 of Japanese Patent Kokai (Laid-Open) No. 59-137851. This membrane contained 10 wt % of tetraoctadecylammonium chloride as a sensitive material, 30 wt % of n-tetradecyl alcohol (carbon number 14), 2 wt % of n-dodecyl alcohol (carbon number 12, melting point 23.5° C.) and 10 wt % of o-nitrophenyloctyl ether as plasticizers and 48 wt % of polyvinyl chloride as a polymer material. That is, the conventional idea of using straight chain aliphatic alcohols differing by two in carbon number was employed and applied to the sensitive material of Example 3.

Comparative Example 6 was based on the anion selective electrode shown in "Mikrochimica Acta", (Wein), 1984 III, 1. This electrode contained 6 wt % of tetradodecylammonium chloride as a sensitive material, 65 wt % of dioctyl sebacate as a plasticizer and 29 wt % of polyvinyl chloride as a polymer material.

Figure 4:
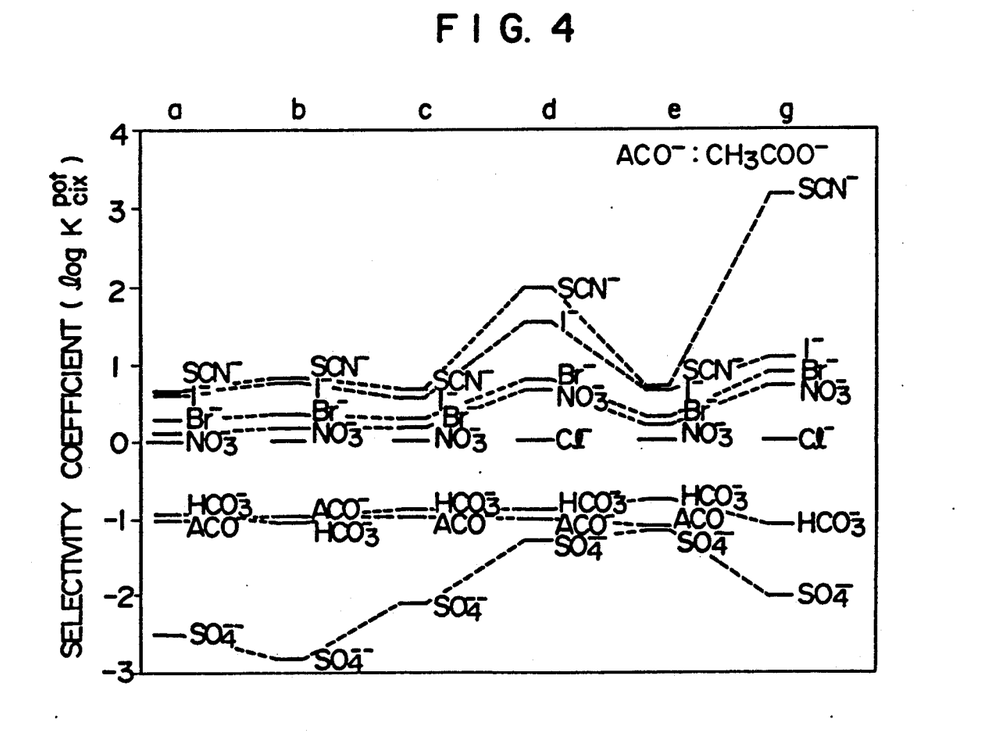
FIG. 4 is a graph which shows the selectivity coefficient of the chloride ion selective electrode of the present invention and a conventional chloride ion selective electrode over various ions.

FIG. 4 shows selectivity coefficients of the chloride ion selective electrodes of Examples 3 and 4 and the conventional electrodes of the above Comparative Examples 2, 3, 4 and 6 over various anions as compared with chloride ions. The selectivity coefficient was measured by the method disclosed in G. J. Moody and J. D. R. Thomas, "SELECTIVE ION SENSITIVE ELECTRODES", published by Merrow Publishing Co., Ltd. In FIG. 4, a and b indicate the results on the electrodes of Examples 3 and 4 and c, d, e and g indicate the results on the electrodes of Comparative Examples 2, 3, 4 and 6, respectively.

As is clear from FIG. 4, the chloride ion selective electrodes of the present invention and the electrode of Comparative Example 2 were markedly improved in selectivity for both the hydrophilic and bulky anions such as sulfate ions ($SO_4^{2-}$) and hydrogencarbonate ions ($HCO_3^-$) and the oleophilic and bulky anions such as thiocyanate ions ($SCN^-$) as compared with other conventional chloride ion selective electrodes. The initial selectivity of the electrode of comparative Example 5 was nearly the same as that of the electrode of the present invention.

Figure 5:
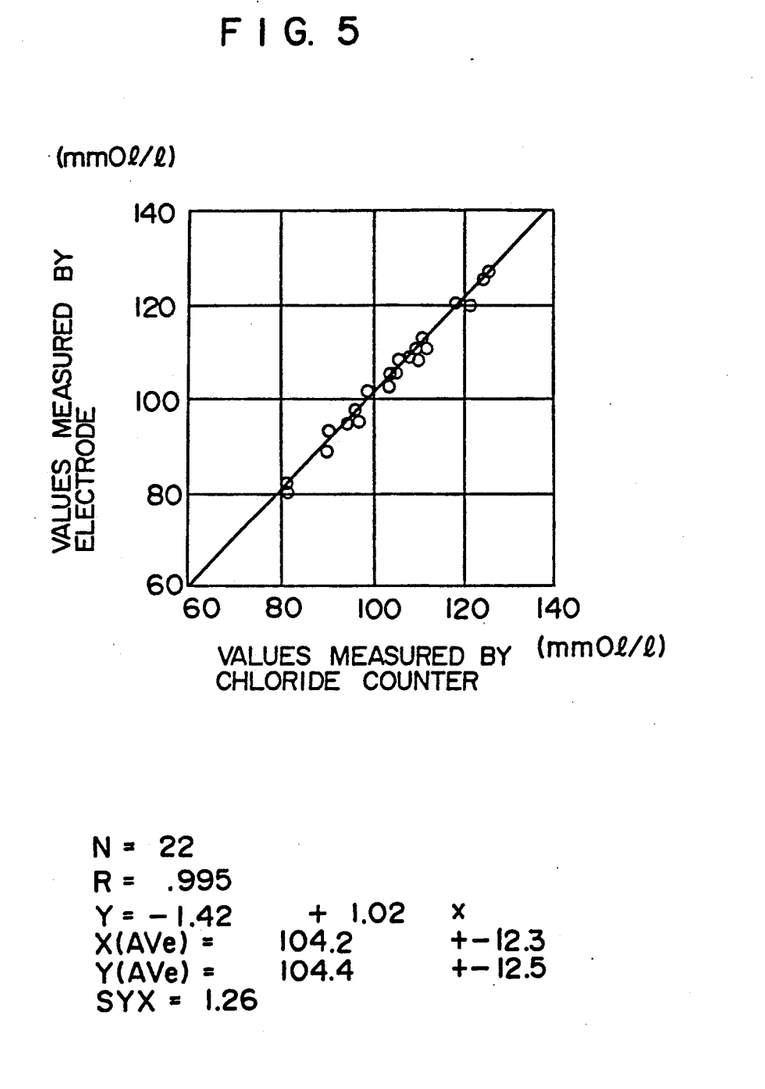
FIGS. 5 and 6 are graphs which show the relation between measured values (on the ordinate axis) according to the chloride ion selective electrode of an example of the present invention and a conventional chloride ion selective electrode and measured values (on the abscissa axis) obtained by a chloride counter according to coulometry.
Figure 6:
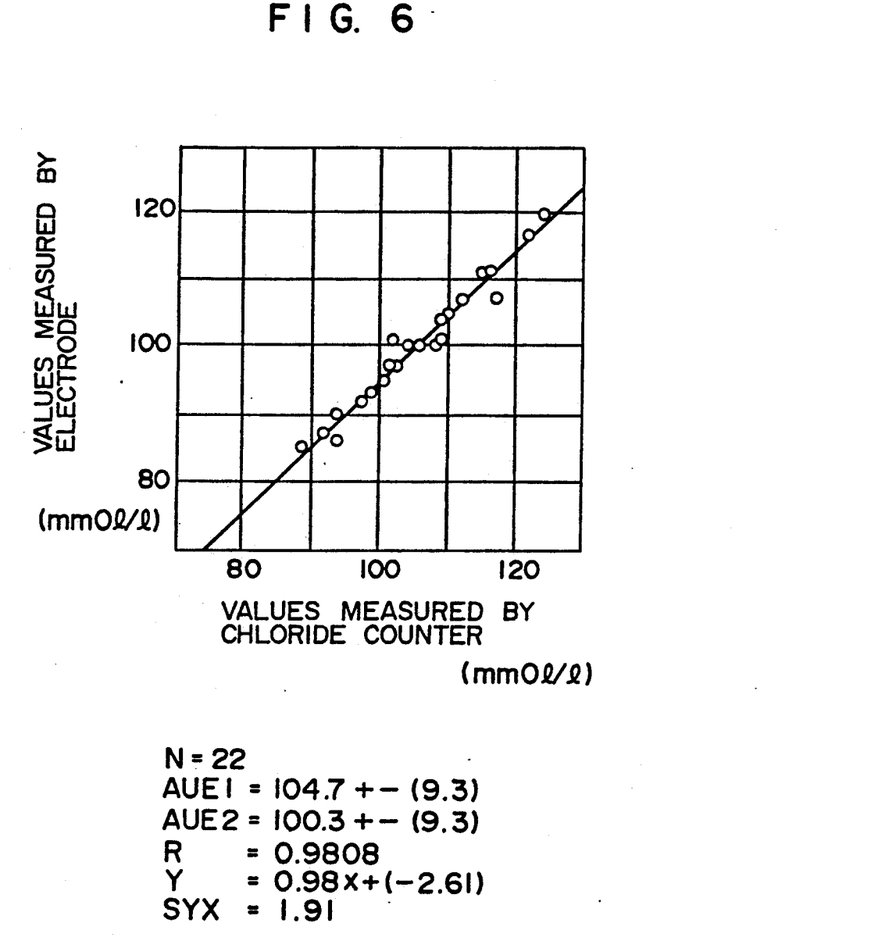

Chloride ion concentration in twenty-two kinds of commercially available controlled blood serums were measured by the chloride ion selective electrode of Example 3 and the correlation between the thus measured values and values measured by a chloride counter which employs the standard method, namely, coulometry was determined. The results are shown in FIG. 5. For comparison, correlation between chloride ion concentration in twenty-two kinds of commercially available controlled blood serums measured by the chloride ion selective electrode of Comparative Example 4 and values measured by the standard method is shown in FIG. 6. As is clear from FIGS. 5 and 6, the chloride ion selective electrode of the present invention is superior in the correlation and less in error free measurement, namely, higher in accuracy.

From the above, it can be seen that the chloride ion selective electrode which contains a tetraalkylammonium salt as a sensitive material and an aliphatic alcohol of low dielectric constant and an organic compound of high dielectric constant has the effects of high selectivity and high accuracy in measurement on serum.

The effects of the present invention in which a mixture of aliphatic alcohols differing by one in carbon number from each other was used as a plasticizer of low dielectric constant will be compared with those of Comparative Example 2 where only one aliphatic alcohol was used and Comparative Example 5 where a mixture of aliphatic alcohols differing by two in carbon number from each other was used.

Impedances of the chloride ion selective electrodes of Examples 3 and 4 according to the present invention and those of the chloride ion selective electrodes of Comparative Examples 2 and 5 are shown in Table 2.

TABLE 2

| Electrode | Impedance (MΩ) |
|---|---|
| Example 3 | 50–400 |
| Example 4 | 50–150 |
| Comparative Example 2 | 1000–14000 |
| Comparative Example 5 | 1200–1900 |

As is clear from Table 2, the electrodes of Examples 3 and 4 according to the present invention are lower by more than about one figure in impedance than the electrodes of Comparative Examples 2 and 5. It can be seen that the electrode of Example 4 is further lower in impedance than the electrode of Example 3 because the former contained aliphatic alcohol of low melting point in a larger amount than in the latter. In application of the electrode to practical measurement, if it has an impedance of higher than 1000 MΩ(1 GΩ), there is the problem that it collects noise that causes scattering of the measured values. The present invention has solved this problem.

Figure 7:
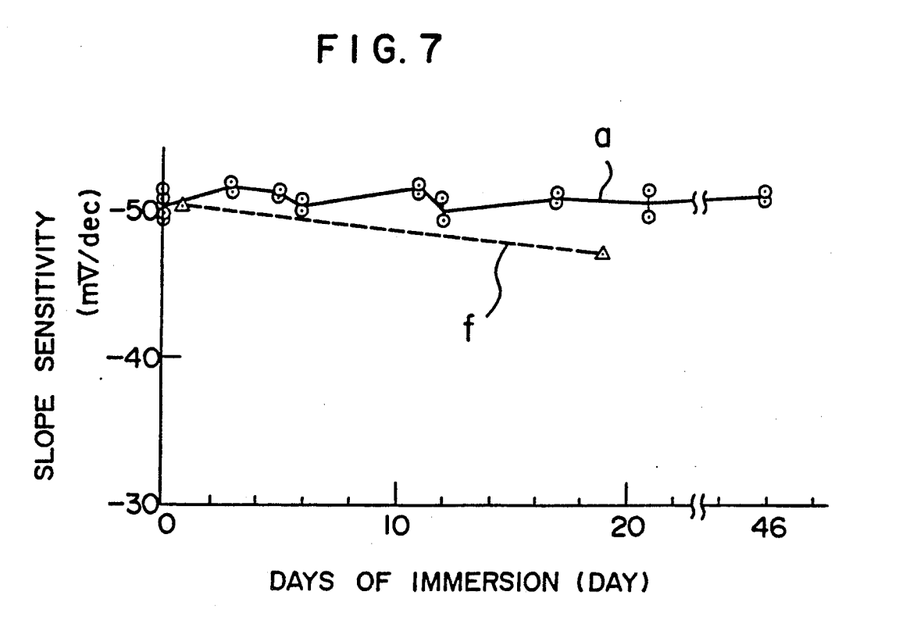
FIG. 7 is a graph which shows change of slope sensitivity of a chloride ion selective electrode of the present invention and a conventional chloride ion selective electrode over a period of days.

Finally, changes of slope sensitivity with lapse of time (in days) of the chloride ion selective electrode of Example 3 and that of Comparative Example 5 were determined by immersing them in aqueous sodium chloride solution of 100 mmol/l. The results are shown in FIG. 7. The slope sensitivity of the chloride ion selective electrode of the present invention was nearly constant for a long period of time as shown by curve a while that of the electrode of Comparative Example 5 decreased in less than the half period as shown by curve f. It is considered that this is because if oleophilicity of the second aliphatic alcohol added is high as in the case of the present invention, it is stably retained in the sensitive membrane while if the oleophilicity is low as in the comparative example, it dissolves out and the electrode performance cannot be stably maintained.

As shown above, the chloride ion selective electrodes according to the present invention are lower in impedance and faster in response time than the conventional electrodes. Besides, the electrodes according to the present invention have the characteristics that the electrode potential is stable and the electrode performance can be retained for a long time. Therefore these electrodes are fully practical as chloride ion selective electrodes.

EXAMPLE 8

In this example, 15 wt % of tetracetylammonium chloride as a sensitive material, 28 wt % of n-tetradecyl alcohol and 2 wt % of tridecyl alcohol as plasticizers of low dielectric constant, 10 wt% of 2-fluoro-2'-nitrodiphenyl ether as a plasticizer of high dielectric constant and 45 wt % of polyvinyl chloride as a polymer material were used for the composition of sensitive membrane 4. The sensitive membrane 4 was formed in the same manner as in Example 1. The carbon number of each alkyl group of the sensitive material in this example was 16, which was smaller by 2 than the carbon number in Example 1. For this reason, in case a sensitive material of high solubility is used, stable electrode characteristics are obtained even when the content of n-tridecyl alcohol is as low as about 2 wt %.

EXAMPLE 9

In this example, bis[di(octylphenyl)phosphato]-calcium which is one of bis[di(alkylphenyl)phosphato]-calcium and has a straight chain alkyl group was used as a sensitive material. Furthermore, 2-fluoro-2'-nitrodiphenyl ether was used as a plasticizer and polyvinyl chloride was used as a polymer material. The 95% response time and the slope sensitivity of the calcium ion selective electrode made by using these membrane materials were substantially the same as those in Example 2.

Similar results can be obtained by using bis[di(hexylphenyl)phosphato]calcium and bis[di-(decylphenyl)-phosphato]calcium as the bis[di(alkylphenyl)-phosphato]calcium compound.

What is claimed is:

1. An ion selective electrode having a sensitive membrane, comprising: a polymer material, an ion sensitive material and a plasticizer, wherein a tetraalkyl ammonium salt or tetraalkylphosphonium salt containing four identical alkyl groups is used as the ion sensitive material, and a compound having the formula (1): wherein x represents an alkyl group, a phenyl group or a phenyl group to which a functional group bonds is used as the plasticizer.

2. An ion selective electrode according to claim 1 wherein said alkyl group in the tetraalkyl-ammonium salt and the tetraalkylphosphonium salt is a straight chain alkyl group.

3. An ion selective electrode according to claim 2 wherein the tetraalkylammonium salt and tetraalkylphosphonium salt have alkyl groups each of which contains 10-24 carbon atoms.

4. An ion selective electrode according to claim 1 wherein the compound having the formula (1) is a 2-nitrophenylalkyl ether and wherein an alkyl group represented by X has 5 or more carbon atoms.

5. An ion selective electrode according to claim 1 and wherein the compound having the formula (1) is a halogen derivative of 2-nitrophenylphenyl ether wherein X is a phenyl group to which a halogen bonds as a functional group.

6. An ion selective electrode having a sensitive membrane, comprising: a polymer material, an ion sensitive material and a plasticizer, wherein the ion sensitive material is a tetraalkylammonium salt or a tetraalkylphosphonium salt having long chained alkyl groups of 10-24 carbon atoms and the plasticizer is a mixture of a compound having the formula (1):

wherein x represents am alkyl group, a phenyl group or a phenyl group to which a functional group bonds and an alcohol compound or an ester compound.

7. An ion selective electrode according to claim 6 wherein the compound having the formula (1) is a 2-nitrophenylalkyl ether and wherein X is an alkyl group of 5 or more carbon atoms.

8. An ion selective electrode according to claim 6 wherein the compound having the formula (1) is a halogen derivative of 2-nitrophenylphenyl ether and wherein X is a phenyl group to which a halogen bonds as a functional group.

9. An ion selective electrode according to claim 7 wherein the alcohol compound is an aliphatic alcohol having a dielectric constant of 10 or less and containing 10 or more carbon atoms.

10. An ion selective electrode having a sensitive membrane, comprising: a polymer material, an ion sensitive material and a plasticizer wherein the ion sensitive material is a tetraalkylammonium salt or a tetraalkylphosphonium salt and the plasticizer is a mixture of a compound having the formula (1):

wherein X represents an alkyl group, a phenyl group or a phenyl group to which a functional group bonds and an alcohol compound or an ester compound, wherein the alcohol compound is an aliphatic alcohol having a dielectric constant of 10 or less and containing 10 or more carbon atoms, and
    wherein the aliphatic alcohol comprises two straight chain alcohols differing from each other by one in the number of carbon atoms.

11. An ion selective electrode having a sensitive membrane, comprising: a polymer material, an ion sensitive material and a plasticizer, wherein the ion sensitive material is a tetraalkylammonium salt or a tetraalkylphosphonium salt and the plasticizer is a mixture of a compound having the formula (1):

wherein X represents an alkyl group, a phenyl group or a phenyl group to which a functional group bonds and an alcohol compound or an ester compound, wherein the alcohol compound is an aliphatic alcohol having a dielectric constant of 10 or less and containing 10 or more carbon atoms, and wherein the aliphatic alcohol comprises two aliphatic alcohols different by 13° C. or lower in melting point from each other.

12. An ion selective electrode according to claim 10 wherein the two straight chain aliphatic alcohols differing by one in the number of carbon atoms are n-tridecyl alcohol and n-tetradecyl alcohol.

13. An ion selective electrode according to claim 6 wherein the sensitive membrane contains 25-60 wt % of a polymer material, 5-30 wt % of a tetraalkylammonium salt as the ion sensitive material, 10-40 wt % of an alcohol compound and 1-30wt % of a 2-nitrophenylalkyl ether or a halogen derivative of 2-nitrophenylphenyl ether as plasticizer.

14. An ion selective electrode according to claim 6 wherein the ion sensitive material is an organic phosphate and the plasticizer is a halogen derivative of 2-nitrophenylphenyl ether.

* * * * *